United States Patent [19]
Chow

[11] Patent Number: 5,176,682
[45] Date of Patent: Jan. 5, 1993

[54] SURGICAL IMPLEMENT

[76] Inventor: James C. Y. Chow, 3001 Carolina St., Mount Vernon, Ill. 62864

[21] Appl. No.: 891,773

[22] Filed: Jun. 1, 1992

[51] Int. Cl.$^5$ .................... A61B 17/56; A61B 17/04
[52] U.S. Cl. ...................................... 606/72; 606/232
[58] Field of Search ............ 606/95, 88, 72, 75, 606/76, 77, 138, 139, 144, 145, 232, 228, 229, 217; 623/13, 16; 411/54, 55, 57, 60, 340, 345, 346

[56] References Cited

U.S. PATENT DOCUMENTS

| | | | |
|---|---|---|---|
| 3,845,772 | 11/1974 | Smith | 606/232 |
| 4,738,255 | 4/1988 | Goble | 606/86 |
| 4,750,492 | 6/1988 | Jacobs | 606/232 |
| 4,898,156 | 2/1990 | Gatturna | 606/232 |
| 4,899,743 | 2/1990 | Nicholson | 606/139 |
| 4,946,468 | 8/1990 | Li | 606/72 |
| 5,041,129 | 8/1991 | Hayhurst | 606/139 |
| 5,046,513 | 9/1991 | Gatturna | 606/72 |
| 5,102,421 | 4/1992 | Anspach | 606/232 |

Primary Examiner—Michael A. Brown
Attorney, Agent, or Firm—Polster, Lieder, Woodruff & Lucchesi

[57] ABSTRACT

A surgical implement (10) for permanently attaching a ligament (L) or a suture to a bone (B). An anchor body (12) is insertable into a pre-drilled hole (H). The outer end of the body is threaded onto a hollow tube (T) which is used to insert the anchor body into the hole. The body has a recess (18) at its inner end for capturing the ligament or suture prior to insertion of the body into the hole. The anchor body has a longitudinally extending bore (14) into which a pin 15 is inserted through the tool. Fins (16a, 16b) on opposite sides of the body extend into the opening in the body but are forced outwardly by the pin as it is inserted in the bore. The fins engage the sidewall of the hole and prevent the anchor body from being dislodged. Because the fins are not pushed outwardly unless the pin is inserted, the anchor body can be trial fit into the hole without it being permanently installed. Thus, if the hole is not suitable, another hole can be drilled and the ligament or suture is permanently attached to the bone only at a suitable site.

18 Claims, 2 Drawing Sheets

5,176,682

SURGICAL IMPLEMENT

BACKGROUND OF THE INVENTION

This invention relates to surgical implements especially those used in arthroscopic surgery, and more particularly, to an anchor for use in permanently attaching ligaments or sutures to a bone.

In certain surgical procedures, for example, those to repair recurrent shoulder dislocations, rotor cuff injuries, or intercrucial ligament repair, it is sometimes necessary to permanently attach a ligament or suture to a bone. Surgical implements, commonly known as suture anchors, are used in these procedures. Such anchors are known in the art as evidenced by U.S. Pat. Nos. 5,046,513; 5,037,422; 4,946,468; 4,898,156; and 4,738,255. Suture anchors typically require a hole to be drilled in the bone. The ligament is then attached to the anchor which is then inserted into the hole. It is a feature of these prior art devices that the ligament or suture attaches to an outer portion of the anchor so that it is affixed to the outside of the anchor regardless of the depth to which the anchor is fitted into the hole. While these anchors are effective for their intended purpose, they do have the drawback in that if the ligament or suture becomes detached from the anchor, the anchor becomes useless and the repair may be jeopardized. A further problem occurs if the hole in the bone in which the anchor is inserted is not satisfactory. Heretofore, suture anchors, once installed in the hole, are permanently in place. Thus, if the hole is unsuitable, further drilling is not only required, but yet another foreign body is introduced at the surgical site. The ligament or suture then has to be detached from the first anchor and attached to the second. Also, with these prior art anchors, the attachment of the ligament or suture must be done outside the body.

SUMMARY OF THE INVENTION

Among the several objects of the present invention may be noted the provision of a surgical implement for use in microsurgery especially arthroscopic surgery; the provision of such an implement which includes an anchor for use in permanently attaching a ligament or suture to a bone; the provision of such an implement having means for permanently affixing the anchor in a hole drilled in the bone specifically to receive the anchor; the provision of such an implement by which the ligament or suture is engaged by the anchor prior to its installation so when the anchor is in place, the ligament is secured between the anchor and the bone thereby to not be subsequently displaced; the provision of such an implement which can be used to attach more than one ligament or suture to the bone at one site; the provision of such an implement by which the anchor can be trial fit in a hole and only permanently installed in the hole if the fit is suitable, but in which the anchor is readily movable to another site if the fit is not suitable; the provision of such an implement by which attachment to a suture or ligament can be done internally rather than externally as with prior art implements; and, the provision of such an implement which is safe and easy to use.

Briefly, a surgical implement of the present invention is for use in permanently affixing a ligament or suture to a bone. As such it is useful to repair repeated shoulder separations, to repair rotator cuff injuries, or in intercrucial ligament surgery. A hole is drilled in the bone. An anchor body is designed to fit in the hole. A hollow, detachable tool is used to position the anchor body in the hole. A transverse slot is formed at one end of the body, and the ligament or suture is captured in this slot prior to inserting the body in the hole. This helps retain the ligament or suture in the bone. If the anchor body properly fits in the hole, a pin is inserted through the tube into a longitudinal bore extending through the anchor body. The pin forces fins formed in the body outwardly to engage the sidewall of the hole. The tool is then detached from the anchor body. If the fit is not suitable, the tool is used to withdraw the body from the hole so it can be installed in the bone at another site. Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
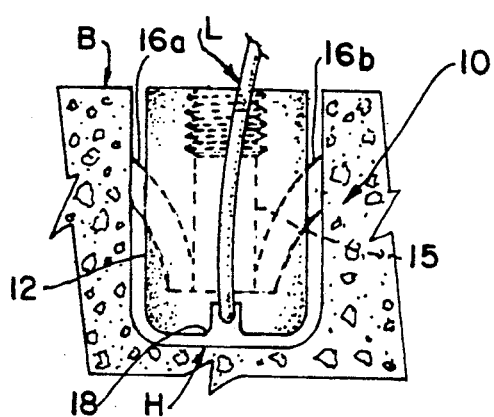
FIG. 1 is a sectional view of the implement of the present invention used to anchor a ligament or suture to a bone.

Referring to the drawings, a surgical implement of the present invention is indicated generally 10. The implement is used to permanently attach a ligament L to a bone B. In addition to the ligament, the implement can also be used to attach a suture to the bone. As such, the implement is useful in surgical procedures such as the repair of dislocations, i.e., shoulder dislocations. Or, it can be used in the repair of rotator cuff injuries. Or, it can be used in intercrucial ligament surgery. In any event, the implement is useful in permanently attaching the ligament or suture to the bone to effect the repair of an injury.

Figure 10:
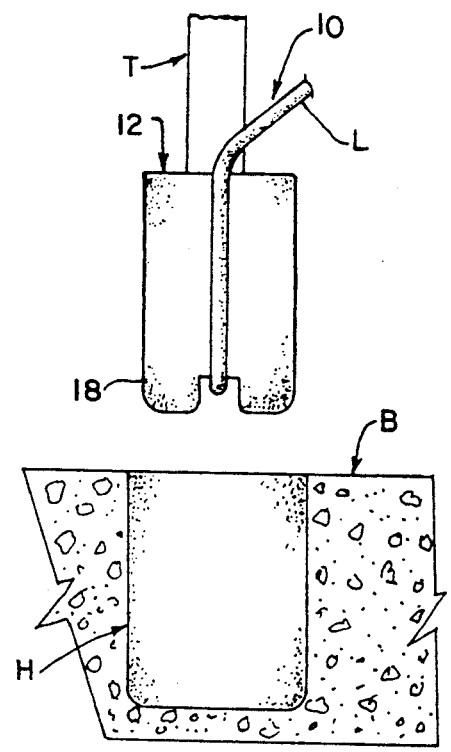
Figure 11:
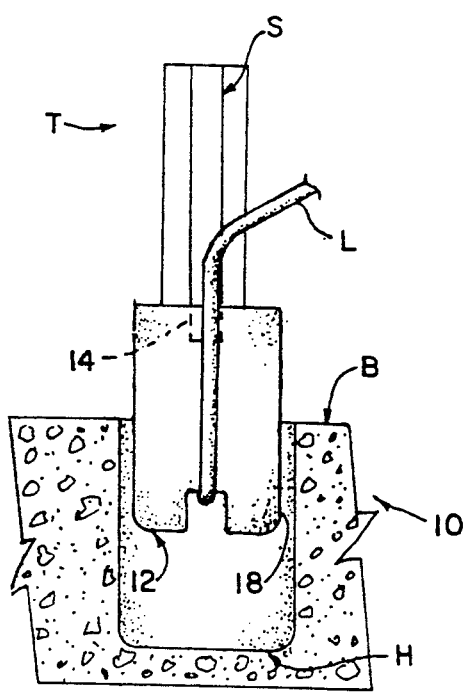
Figure 12:
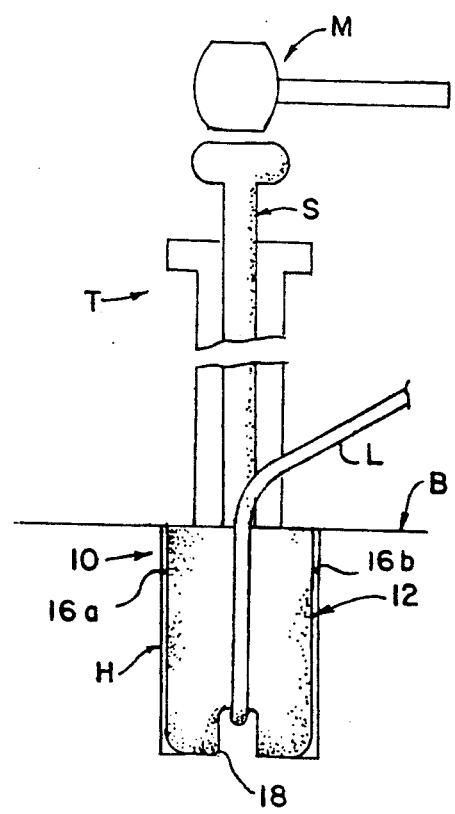

Implement 10 includes a cylindrical body 12 which is sized to be received in a hole H drilled in the bone. The body may be of any suitable material which can be permanently retained in the body. The body has a longitudinal central bore 14. The outer end of bore 14 is threaded. A hollow tool T is matingly attached to body 12 by being threaded into bore 14 (see FIGS. 10–12).

Figure 2:
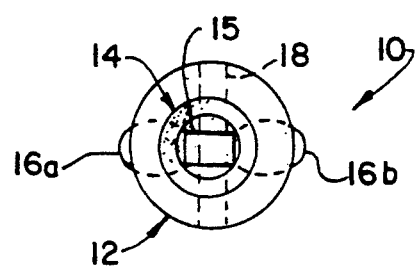
FIGS. 2–4 are respective top and side views of the implement.
Figure 3:
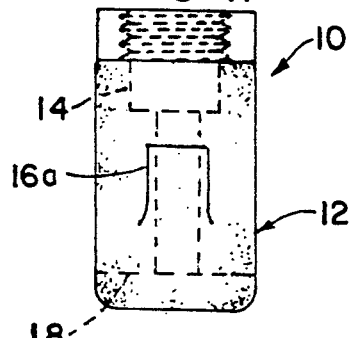
Figure 4:
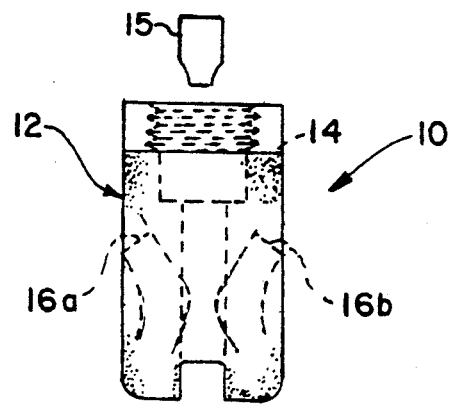
Figure 6:
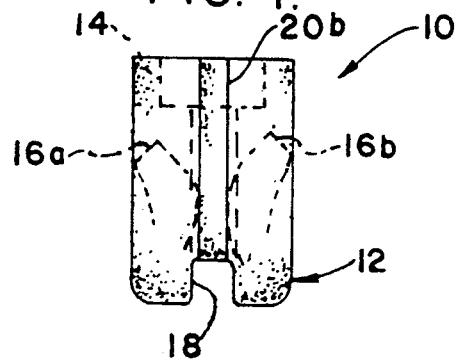

Integrally formed with body 12 are opposed fins 16a and 16b respectively. The lower end of the fins extend into bore 14 as shown in FIGS. 2, 4 and 6. The fins curve outwardly from body 12. A pin 15 (see FIGS. 1 and 4) is insertable in bone 14. Fins 16a, 16b are flexible so that as pin 15 is driven into bore 14, the fins are forced outwardly. For this purpose, the base of pin 15 may be beveled to provide an angled or curved contact surface between the pin and the fins. When the pin is in place, the fins press outwardly against the sidewall of the hole. The force exerted by the fins prevent the body from becoming dislodged.

The inner end of body 12 has a transversely extending recess 18. The outer ends of the recess are orthogonal to the fins. A ligament L or suture to be captured in the bone is caught in the recess prior to the body being inserted in the hole (see FIG. 10). The portion of the ligament captured in the recess is intermediate the length of the ligament so portions of the ligament extend out of the hole on either side of the body.

Figure 5:
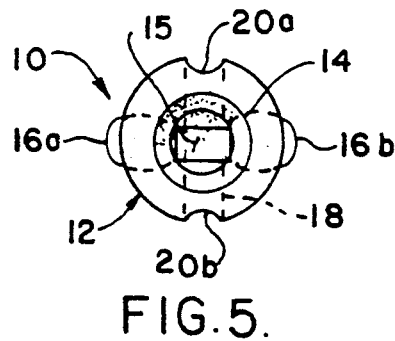
FIGS. 5 and 6 are respective top and side views of a second embodiment of the implement.

As shown in FIGS. 5 and 6, opposed channels 20a, 20b extend longitudinally of the body on either side thereof. The inner ends of the channel open into recess 18 for the ligament to rest in the channels and the recess.

Figure 7:
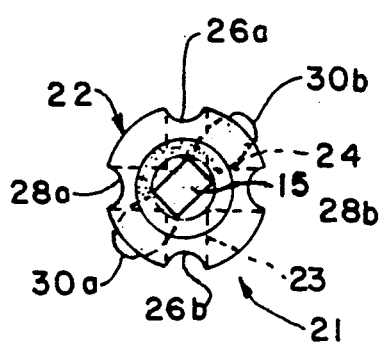
FIGS. 7 and 8 are respective top and side views of a third embodiment of the implement.
Figure 8:
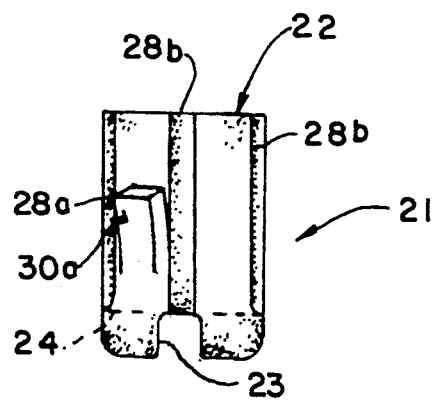
Figure 9:
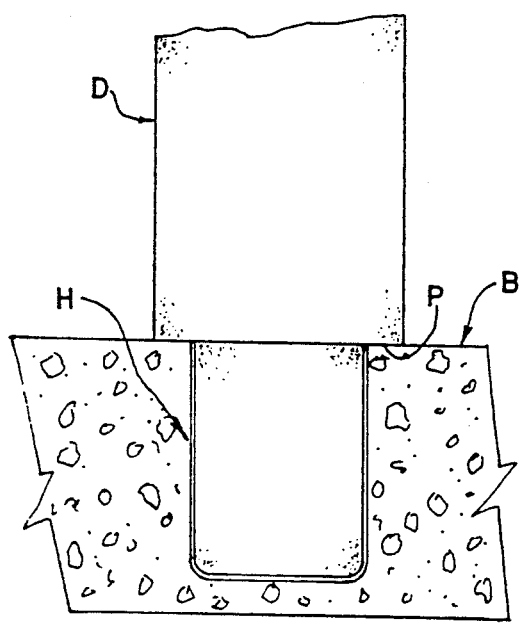
FIGS. 9–12 illustrate the sequence of steps for drilling a hole in a bone and installing the implement, with the ligament attached, therein.

Referring to FIGS. 7 and 8, a second embodiment of the implement is indicated generally at 21. Implement 21 has a body 22 with intersecting recesses 23, 24 at its inner end. This allows two ligaments or sutures to be captured by the implement prior to insertion in the hole. Implement 21 has two sets of opposed channels 26a, 26b, and 28a, 28b in which the respective ligaments or sutures can run. The implement also has opposed fins 30a, 30b which function in the same manner as fins 16a, 16b.

Referring to FIGS. 9-12, a drill D is used to drill a hole H in the bone. The drill has a stop P to limit the depth to which the hole is drilled so it has a predetermined size and depth. After drilling, tool T is threaded into the threaded end of body 14. Next, the body is maneuvered until ligament L is captured in recess 18 of the body. The body is then inserted in hole H. If the body with the attached ligament or suture properly fits in the hole, pin 15 is inserted into bore B through the hollow center of tool T. A mallet S is then inserted into the tool so its inner end bears against pin 15. A hammer H is then used to tap against the outer end of the mallet to drive pin 15 down bore 14. Movement of the pin forces fins 16a, 16b outwardly against the sidewall of the hole. Tool T is then disconnected.

Because the ligament or suture is captured in recess 18 and thus is held in place by body 12, it cannot be dislodged. This is unlike prior suture anchors in which the ligament is held on the outer end of the anchor. Since the anchor is intended to permanently hold the ligament to the bone, if the ligament breaks loose, which it may, it must be re-anchored. This would require additional surgery. Such an event is prevented by implement 10 of the present invention.

On the other hand, if body 12 does not fit in the hole, it is readily removed. The body can then be moved to a new hole, or a new hole H can be drilled and the implement inserted into it. Again, this is unlike prior art anchors which are permanently in place once installed in a hole in the bone.

In view of the foregoing, it will be seen that the several objects of the invention are achieved and other advantageous results are obtained.

As various changes could be made in the above constructions without departing from the scope of the invention, it is intended that all matter contained in the above description or shown in the accompanying drawings shall be interpreted as illustrative and not in a limiting sense.

Having thus described the invention, what is claimed and desired to be secured by Letters Patent is:

1. A surgical implement for use in anchoring a ligament or suture to a bone comprising:
an anchor body sized to fit in a hole drilled in the bone to receive the body;
attachment means integrally formed with the body for attaching the body permanently to the bone;
means formed on the inner end of the body for capturing a ligament or suture prior to insertion of the body into the hole and for retaining the ligament or suture in place thereafter; and,
means insertable into the body once the body is in the hole for engaging the attachment means to attach the body to the bone.

2. The implement of claim 1 wherein the body has a longitudinal bore extending therethrough and the insertable means comprises a pin insertable into the bore.

3. The implement of claim 2 wherein the attachment means includes a plurality, of fins formed in the body and extending into the bore, said pin, when inserted into the bore, pushing against the fins and forcing them outwardly to engage the bone and thereby attach the body to the bone.

4. The implement of claim 3 wherein the inner end of the body has a transverse slot for capturing the ligament or suture and holding it in place when the body is inserted in the bone.

5. The implement of claim 4 further including opposed grooves extending along the sidewalls of the body, the ligament or suture fitting in the grooves.

6. The implement of claim 5 wherein the inner end of the body has a pair of transverse grooves orthogonal to each other for a separate ligament or suture to be captured in each groove.

7. The implement of claim 6 including opposed sets of slots extending the length of the body, each of the ligaments or sutures fitting in the respective sets of slots.

8. The implement of claim 3 further including means on the outer end of the body for inserting the body into the hole.

9. The implement of claim 8 wherein the outer end of said longitudinal bore is threaded for a tool with mating threads to be removably connected to the body to insert the body into or withdraw it from the hole, the tool not being removed until after the using surgeon determines the hole in which the body is inserted is acceptable, and the pin is installed in the body.

10. A surgical apparatus for anchoring a ligament or suture in a bone structure comprising:
means for drilling a hole in a bone;
an anchor body insertable in the hole and including means for capturing the ligament or suture prior to insertion of the anchor body into the hole and means for permanently attaching the anchor body to the bone;
means insertable into the anchor body for engaging said attaching means and forcing them into engagement with the bone to attach the anchor body to the bone; and,
means removably attachable to the anchor body for inserting the anchor body into the hole and holding it in place while the insertable means is being inserted in the anchor body, whereby if the hole is suitable, the anchor body can be permanently installed therein, but if not suitable, the anchor body can be withdrawn and moved to a new hole site.

11. The apparatus of claim 10 wherein the drilling means includes a drill for drilling a hole of a predetermined size and depth in the bone.

12. The apparatus of claim 10 wherein said anchor body is sized to be received in said hole and has a transversely extending slot at its inner end for capturing the ligament or suture prior to insertion of the anchor body into the hole.

13. The apparatus of claim 12 wherein the anchor body has a longitudinally extending bore and a plurality of fins integrally formed with the body and extending into the bore.

14. The apparatus of claim 13 wherein said insertable means includes a pin insertable in the bore after the anchor body has been installed in the hole, said pin forcing said fins outwardly as it is inserted through the bore, the outer end of said fins engaging the sidewall of the hole as they are forced outwardly thereby to attach the anchor body to the bone.

15. The apparatus of claim 14 wherein the outer end of said anchor body is threaded and said means removably attachable to said anchor body includes a hollow tool matingly threaded at its lower end for attachment to said anchor body to insert said anchor body into said hole and maintain it there, said pin being insertable into the bore through the hollow portion of the tool, and said tool being detached from said anchor body after insertion of the pin.

16. A method for arthroscopic surgery to permanently attach a ligament or suture to a bone comprising:
   drilling a hole of predetermined size and depth into a bone;
   attaching a tool to the outer end of an anchor body which is sized to be received into the hole;
   capturing a section of the ligament or suture in a recess formed in the other end of the anchor body from which the tool is attached;
   inserting said anchor body into said hole using said tool and determining if the anchor body properly fits in said hole;
   withdrawing said anchor body from said hole if said anchor body does not properly fit; but, if the anchor body does properly fit, inserting a pin into said anchor body to attach said anchor body to said bone; and,
   detaching said tool from said anchor body after said anchor body is attached to said bone.

17. The method of claim 16 wherein said tool is hollow and said anchor body has a longitudinal bore, and attaching said anchor body to said bone includes inserting said pin into said longitudinal bore through said tool.

18. The method of claim 17 wherein said anchor body further includes integrally formed fins which extend into said longitudinal bore, and attaching said bone further includes forcing said fins outwardly upon insertion of said pin through said bore for the outer end of said fins to engage the sidewall of the hole.

* * * * *